United States Patent
Braginsky et al.

(10) Patent No.: US 6,260,696 B1
(45) Date of Patent: Jul. 17, 2001

(54) SUTURE PACKAGE

(75) Inventors: Michael Braginsky, Newton; Joan P. Goldberg, Somerset, both of MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/542,215

(22) Filed: Apr. 4, 2000

Related U.S. Application Data
(60) Provisional application No. 60/129,651, filed on Apr. 16, 1999.

(51) Int. Cl.[7] .................................................... A61B 17/06
(52) U.S. Cl. ........................................... 206/63.3; 206/380
(58) Field of Search ................................ 206/63.3, 380, 206/482, 483, 495

(56) References Cited

U.S. PATENT DOCUMENTS

| | | |
|---|---|---|
| D. 272,600 | 2/1984 | Kubas . |
| 2,281,236 | 4/1942 | Eckman . |
| 3,341,066 | 9/1967 | Bowes . |
| 3,363,751 | 1/1968 | Shave et al. . |
| 3,444,994 | 5/1969 | Kaepernik et al. . |
| 3,556,620 | 1/1971 | Gutierrez . |
| 3,779,375 | 12/1973 | Foster . |
| 3,834,778 | 9/1974 | Morrison et al. . |
| 3,857,482 | 12/1974 | Shelton . |
| 4,014,434 | 3/1977 | Thyen . |
| 4,034,850 | 7/1977 | Mandel et al. . |
| 4,120,395 | 10/1978 | Mandel et al. . |
| 4,121,711 | * 10/1978 | Bolanowski ..................... 206/63.3 |

(List continued on next page.)

FOREIGN PATENT DOCUMENTS

| | | |
|---|---|---|
| 2096657 | 6/1999 | (CA) . |
| 1290296 | 3/1969 | (DE) . |
| 1935364 | 11/1970 | (DE) . |
| 27 17 537 | 10/1978 | (DE) . |
| 3027836 | 3/1982 | (DE) . |
| 197 06 729 | 8/1998 | (DE) . |
| 197 43 453 A1 | 4/1999 | (DE) . |
| 0168172 | 1/1986 | (EP) . |
| 0498460 | 8/1992 | (EP) . |
| 2374016 | 7/1978 | (FR) . |
| WO 95/08302 | 3/1995 | (WO) . |
| WO 98/27871 | 7/1998 | (WO) . |

*Primary Examiner*—David T. Fidei
(74) *Attorney, Agent, or Firm*—Richard D. Allison; Thomas J. DesRosier (57) ABSTRACT

The present invention provides a suture package and packaging method which ensures rapid access to sutures, one at a time, from a suture package which is easy to handle and store. Each suture is readily located in an advantageous position in the package, to be grasped by a needle holder, without the possibility of pulling unwanted sutures from the package, or the need to fumble through a bunch of needles to ensure that a single suture is obtained. This is done by providing a suture package, comprising a panel or panels having an open window to expose the needles, and a plurality of raised support elements on at least one side of the panel, which elements support a suture in conjunction with the panel, the support elements being arranged to permit withdrawal of a suture from the package by pulling one end of the suture in a direction parallel to the plane of the panel. The needle window opening is located on the top edge of the package, exposing the needles in the opening, and showing the number of sutures available, as well as allowing access to the needles. Preferably, the suture package also employs at least one panel which has support elements for supporting sutures on each side of the panel. Preferably, the panels comprise separate needle window openings for the sutures on each side, and those needle window openings are separated from each other, so that the withdrawal of the suture will withdraw only one suture and in the assembled package, the windows on each panel line up with each other.

21 Claims, 5 Drawing Sheets

U.S. PATENT DOCUMENTS

| | | |
|---|---|---|
| 4,135,623 | 1/1979 | Thyen . |
| 4,253,563 | 3/1981 | Komarnycky . |
| 4,261,463 | 4/1981 | Shave . |
| 4,391,365 | 7/1983 | Batchelor . |
| 4,483,437 | 11/1984 | Cerwin et al. . |
| 4,615,435 | 10/1986 | Alpern et al. . |
| 4,708,241 | 11/1987 | Black . |
| 4,896,767 | 1/1990 | Pinheiro . |
| 5,024,322 | 6/1991 | Holzwarth . |
| 5,024,324 | 6/1991 | Whittaker . |
| 5,123,528 | 6/1992 | Brown et al. . |
| 5,127,518 * | 7/1992 | Holzwarth et al. ............... 206/63.3 |
| 5,197,597 * | 3/1993 | Leary et al. ...................... 206/63.3 |
| 5,199,561 | 4/1993 | Roshdy et al. . |
| 5,249,672 | 10/1993 | Brown et al. . |
| 5,279,411 | 1/1994 | Brunken . |
| 5,282,533 | 2/1994 | Holzwarth et al. . |
| 5,312,250 | 5/1994 | Ellman et al. . |
| 5,335,775 | 8/1994 | Scanlon et al. . |
| 5,344,005 * | 9/1994 | Kettner et al. ..................... 206/63.3 |
| 5,413,214 | 5/1995 | Schonke . |
| 5,582,288 | 12/1996 | Zatarga . |
| 5,662,228 | 9/1997 | Mendoza et al. . |
| 5,788,062 * | 8/1998 | Cerwin et al. ..................... 206/63.3 |
| 5,848,714 | 12/1998 | Robson et al. . |
| 6,080,184 * | 6/2000 | Peters et al. ....................... 606/232 |

* cited by examiner

SUTURE PACKAGE

The present application is related to U.S. Ser. No. 60/129,651 filed on Apr. 16, 1999 the priority thereof is claimed hereby and the disclosures thereof are incorporated herein by reference.

FIELD OF THE INVENTION

The present invention relates to packages for storing and dispensing surgical needles and attached suture filaments. More particularly, it relates to a package for dispensing metallic sutures bearing surgical needles, which package is easier to store, easier to dispense and the sutures obtained therefrom are easier to use.

BACKGROUND OF THE INVENTION

A number of packages and packaging methods have been proposed over the years for economically and reliably delivering or relaying an "armed" suture i.e., a suture having a surgical needle attached, to a surgeon in a sterile condition. Besides maintaining sterility of the armed suture, its packaging must also provide convenient dispensing of the suture under the demanding conditions of surgery. Some of the systems proposed are the subject of U.S. Pat. No. 4,967,902 to Sobel et al., U.S. Pat. No. 5,052,551 to Cerwin et al, and U.S. Pat. No. 5,887,706 to Pohle et al. Those patents disclose generally oval suture packages, having a central needle park for holding or "parking" the surgical needle and a peripheral channel for receiving the suture filament attached to the needle. The clearance between successive filament loops and the suture channel, the shape of the channel, and the material composition of the package, are said to be designed so that the suture can be withdrawn from the package without binding in the suture channel.

Because of the widespread use of armed sutures, their packaging and production occurs on a large scale, such that small changes in their design and/or production methods can generate large implications in terms of the expense and efficiency of production, as well as energy and material costs.

Particular problems are associated with armed metallic sutures, such as sternotomy closure sutures. These are used to rejoin ("approximate") the sternum following open chest surgery. The procedure in which the sternum is opened, usually by means of a specially designed surgical saw, is known as a median sternotomy. The act of closing the sternum is termed a sternotomy closure. This must be done with very strong and reliable suture material.

The procedure typically involves the passing of the needle attached to the stainless steel suture through the solid bony structure of each side of the separated parts of the sternum, tightening the joined sternum structure, and ultimately twisting the suture so that the joined sternum will not move during the healing process. In some instances, the suture is passed around one or both parts of the separated sternum and then tightened by twisting the wire suture.

After the suture is adequately tightened, the ends of the suture are cut off, and the portion of the twisted suture bearing the cut ends is bent to be in contact with the joined sternum, so that the cut ends do not injure other tissues. The sutures are left in the patient, and continue to provide support, even after the portions of the sternum have grown back together and healed.

The procedure typically involves the application of a number of sutures along the length of the sternum.

Stainless steel sutures are the sutures of choice for such applications. Stainless steel sutures have extremely high tensile strength relative to its diameter. It is a monofilament suture material which is inert in tissue. When implanted in areas of infection, stainless steel sutures will not split spontaneously, nor necessitate removal in order for wound healing to occur.

The application of the sutures involves stressful twisting, lifting and tightening of the suture material in order to provide a secure closure of the patient's chest. For adequate healing of the sternum, the sutures must hold the portions of the sternum together throughout the healing process. Coughing and other patient movements can put tremendous stress on the sternum, and thus on the sutures during the healing process. If the sutures are not tightened sufficiently to hold the bone portions together tightly during such stressful conditions, proper healing may not take place, resulting in unnecessary pain for the patient, and sometimes necessitating reopening the wound, re-breaking of the sternum, and setting new sutures to support the healing process.

For that reason, the sutures are preferably twisted to very high tightness. Often they are twisted to the point where the surface patina of the suture material changes, indicating a close approach to the maximum tensile strength of the material.

The required manipulations of sternotomy sutures necessitate that the length of the sutures used must be far in excess of the length of the suture material left in the patient. Surgeons commonly require sternotomy sutures greater than twelve inches long for use with adults.

Until now, sternotomy sutures have been sterilely packaged in long cardboard envelopes, typically 19 to 22 inches in length. Those envelopes are overwrapped with a chevron sleeve made of plastic films joined in a manner which maintains sterility within the sleeve, but permits separation of the films to permit access to the sterile cardboard straight pack in the sterile filed of the operating room. Each straight pack contains the number of sutures needed for the operation, with the needle ends of the sutures placed at the opening end of the envelope.

The size of these stainless steel sutures, and the manner of their packaging have caused problems in the past. Normally, prior to surgery, a surgical nurse has to go in and pull all sutures needed for the case, and work them on to the sterile field, ready to go into the surgeon's hand. Typically open the covering flap, tear off the top, and place the opened package on a sterile Mayo stand, along with all of the other sterile products to be used during the operation.

During surgery, the sutures must be provided, one at a time, on demand. The sutures are pulled from the straight pack and placed in a needle holder, for application to the sternum. Working with surgical gloves, it is easy to grab more than on suture or needle. Extraction of the suture from the straight pack may cause one or more other sutures to accompany it out of the pack. If a suture falls out of the sterile field, it must be re-sterilized or replaced. Wire sutures are also more difficult to handle than other suture materials, since both the needle end and the tail end of the suture have the capability to pierce surgical gloves, which also wreaks havoc on the sterile field. Time is often crucial in open chest surgery, so each delaying or disrupting factor can have substantial influence on the outcome.

Wire sutures also have a tendency to kink or undergo plastic deformation, which forms weak points in the suture, leading in some cases to broken stainless steel wires inside patients, which necessitates reopening of the wound and correction of the problem.

SUMMARY OF THE INVENTION

The present invention provides a suture package and packaging method which ensures rapid access to sutures, one at a time, from a suture package which is easy to handle and store. Each suture is readily located in an advantageous position in the package, to be grasped by a needle holder, without the possibility of pulling unwanted sutures from the package, or the need to fumble through a bunch of needles to ensure that a single suture is obtained.

Moreover, the manner in which the suture is supplied in accordance with the present invention tends to ensure that the sutures provided are in a sterile conditions, and without kinks or other deformities which might adversely effect their strength.

The length of the package is reduced approximately in half, by curving the suture so that its length is substantially reduced. The bending is carried out over a form, in such a manner that the minimum radius of the bend is such that the tensile strength of the suture is not substantially reduced. Thus simply bending the suture in half would induce a kink in the structure, which would substantially reduce the tensile strength. Instead, the suture is subjected to a curve, and is so held in and delivered from the suture package of the present invention. The curve is preferably approximately U-shaped, and is determined in such a way that the minimal radius of curvature to which the suture is subjected is not one which would substantially adversely effect the tensile strength of the suture. This can easily be determined experimentally for any suture of any particular length and diameter. Preferably it is determined by deforming the suture material around mandrels having different radii of curvature, and observing the surface under a scanning electron microscope for surface damage, particularly on the surface of the inside of the curvature. Preferably, the surface merely shows strain hardening, without producing cracks. Under that procedure, the minimum radius of curvature for stainless steel sutures having size of 6 is about 0.5 inches. Preferably the minimum radius of curvature is substantially above that size, e.g., about 1 to 1.5 inches, or greater.

The present invention also provides sutures which are individually presented, in a manner which minimizes the opportunity for pulling more than one suture from the package at a time, and which is much easier and more efficient than the prior packaging for such sutures. This is done by providing a suture package, comprising a panel or panels having an open window to expose the needles, and a plurality of raised support elements on at least one side of the panel, which elements support a suture in conjunction with the panel, the support elements being arranged to permit withdrawal of a suture from the package by pulling one end of the suture in a direction parallel to the plane of the panel. The needle window opening is located on the top edge of the package, exposing the needles in the opening, and showing the number of sutures available, as well as allowing access to the needles.

Preferably, the suture package employs at least one panel which has support elements for supporting sutures on each side of the panel. Preferably, the panels comprise separate needle window openings for the sutures on each side, and those needle window openings are separated from each other, so that the withdrawal of the suture will withdraw only one suture. In the assembled package, the windows on each panel line up with each other.

A preferred embodiment of the package employs a plurality of panels, joined together, so that the number of sutures to be utilized in a particular operation can be supplied together in a sterile package. Preferably, the assembly of panels is attached to a cover, which covers the sutures mounted on the front and back panels of the assembly, and can be removed when the sutures are to be used.

Once the sutures are assembled in the package of the present invention, the sterile package is overwrapped with a sterile barrier such as a Mylar®/Tyvec® (pouch, which is impervious to germs, and which will have sufficient strength to be handled and stored without loss of sterility of the interior pack, and one which can be easily opened during transfer to the sterile field of an operation.

It is most preferred that the suture package of the present invention be included in a package with all single use products necessary for performing cardiac or other surgery. Until the present invention, which has enabled the package length for sternotomy sutures to be reduced approximately in half, it was not possible to include such sutures in one easily accessible package with the other materials necessary for the operation. Other products which can be included in the overall package are, for example, other needled and non-needled suture products and disposable surgical instruments.

BRIEF DESCRIPTION OF THE FIGURES

A better understanding of the present invention may be had by consideration of the following description of an illustrative embodiment thereof, taken in conjunction with the attached drawings, in which.

DETAILED DESCRIPTION OF THE ILLUSTRATIVE EMBODIMENT

Figure 1:
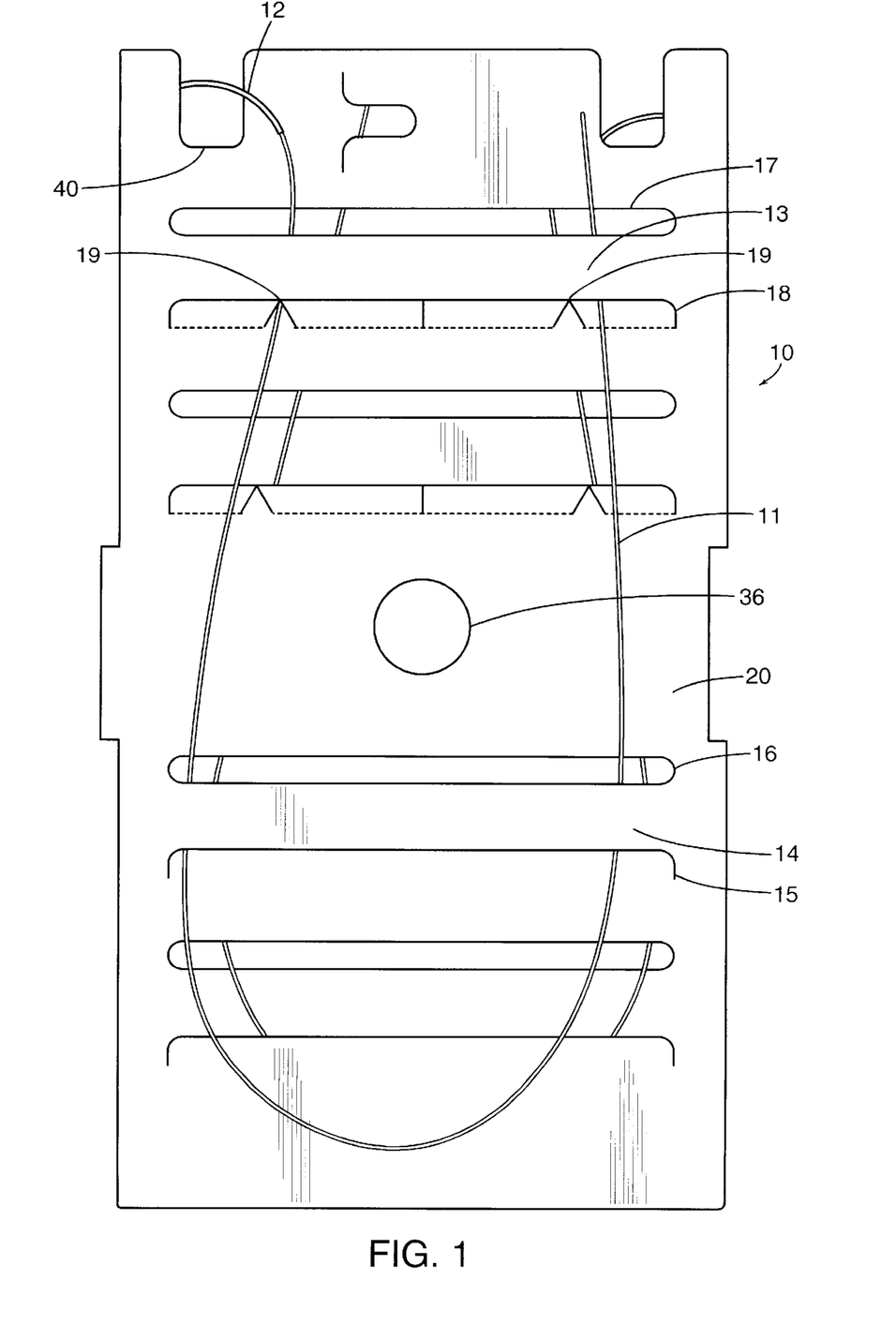
FIG. 1 is a plan view of one face of a suture holder in accordance with the invention.

FIG. 1 depicts a suture holder or package 10, comprising a cardboard panel 20, bearing a stainless steel sternotomy suture 11. The suture 11 illustrated is 18 inches (45 cm) long, and has a thickness of 5 French (7 metric). It has been bent into a U-shaped curve, the minimum radius of which is about 1.5 inches, substantially larger than the minimum curve which would substantially adversely impact the tensile strength of the suture. The suture 11 has a sternotomy K ⅜ circle needle 12 at one end, attached to the stainless steel suture by crimping.

The panel has two raised support elements, 13 and 14, formed from the panel material by making cuts in the panel. As illustrated, below support member 14, the panel has been cut to form a slit 15, through which the suture 11 is placed. The slit 15 and support elements 13 and 14 tend to hold the suture in place until removed by the operating room personnel. Above support member 14, the panel has been cut to form an oblong opening 16.

Similarly, above support member 13, the panel has been cut to form an oblong opening 17, and below support member 13 the panel has been cut to form a flap 18. Preferably, the flap 18 is provided with placement notches 19, in order to guide the placement of the suture in the package, and preferably to hold the suture in a preferred position in the package.

In manufacturing, the suture is formed into the desired curve, e.g., by bending around a mandrel, and then inserted between the support members 13, 14 and 19, and the face of the panel. The support members 13, 14 and 19 contact the suture and hold it against the remainder of the panel surface while the package is sterilized, transported, stored, etc. Preferably, flap 18 is provided with placement notches 19 in order to guide the placement of the suture in the package, and preferably to hold the suture in the preferred position in the package.

When the suture is to be used, it is easily removed from the package by grasping one end of the suture or needle and pulling the suture upwardly. The removal of the suture is greatly facilitated by the window opening 40. For example, the surgeon or surgical nurse can place a finger or needle holder into the needle window 40, under the needle 12, and pull the suture out of the package by the needle end. The needles are staggered so that only one needle is presented at a time. The possibility of tangling or pulling more than one suture out of the package at once is avoided. The package is relatively short, and easily accommodated on the Mayo table along with other items to be used in the operation. The process of getting the suture to the surgeon, with the needle ready for application to the patient, is vastly simplified, compared to prior approaches.

Preferably the package is designed so that the panel can hold a plurality of sutures and needles. This is preferably done by forming an additional plurality of support members on the opposite side of the panel.

Figure 2:
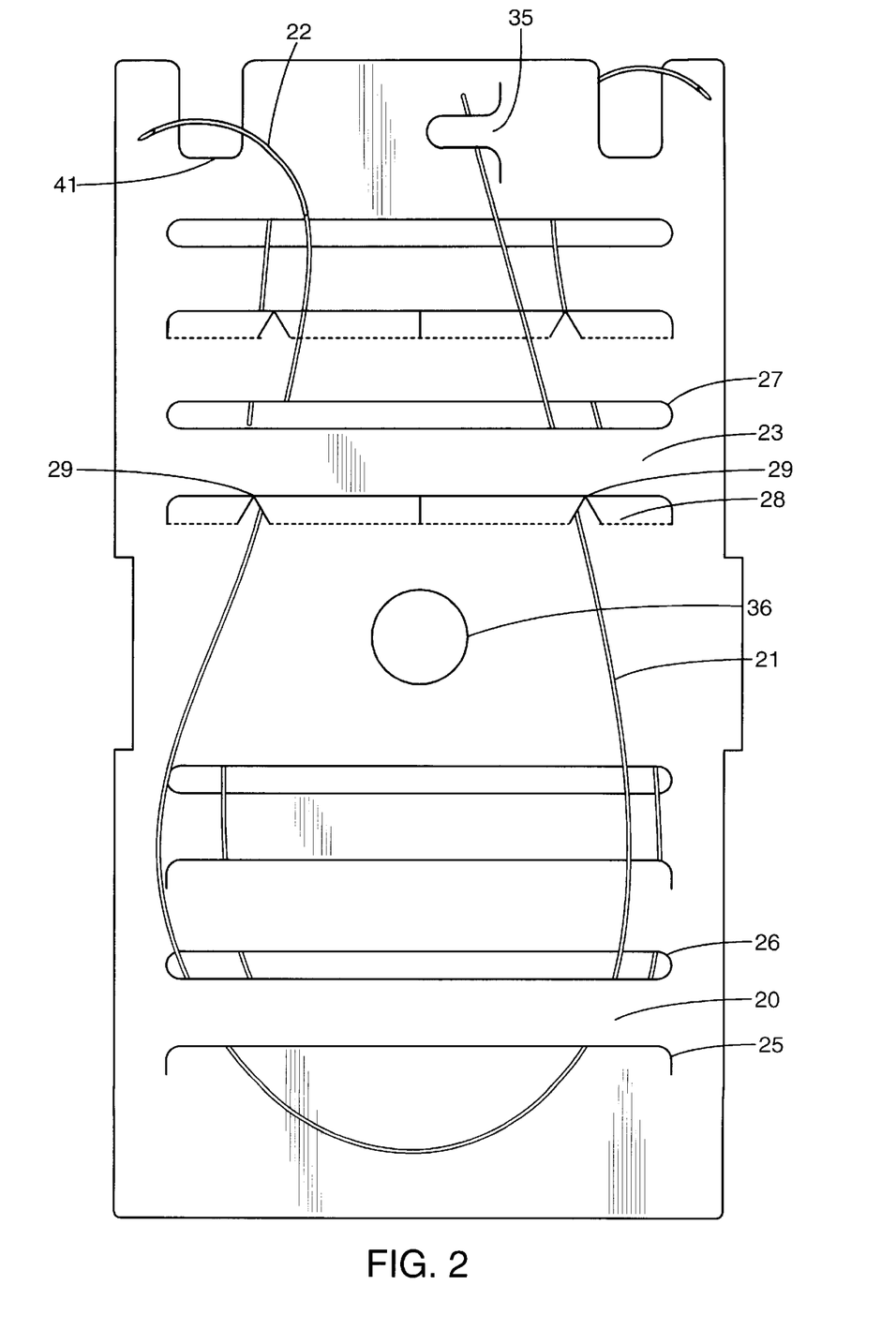
FIG. 2 is a plan view of the opposite face of a suture holder in accordance with the present invention.
Figure 3:
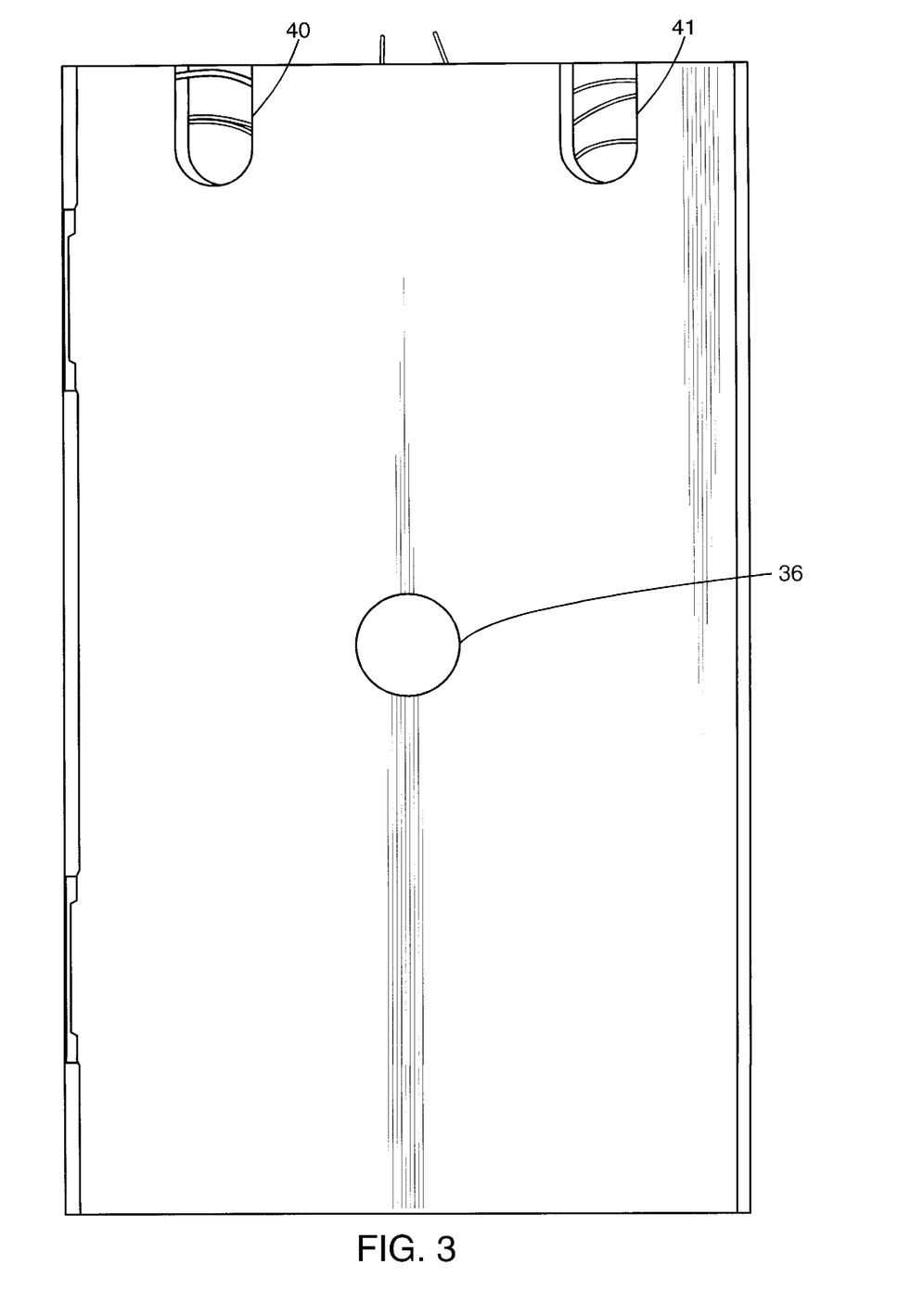
FIG. 3 is a plan view of the back cover of a suture package containing a plurality of panels as illustrated in FIGS. 1 and 2.

FIG. 2 shows the opposite side of the panel package 10 from FIG. 1. The cardboard panel 20, bearing a second stainless steel sternotomy suture 21, which, as illustrated, is also is 18 inches (45 cm) long, and has a thickness of 5 French (7 metric). It has likewise been bent into a U-shaped curve, the minimum radius of which is about 1.5 inches, substantially larger than the minimum curve which would substantially adversely impact the tensile strength of the suture. The suture 11 has a sternotomy K ⅜ circle needle 22 at one end, attached to the stainless steel suture by crimping.

The panel has two raised support elements, 23 and 24, formed from the panel material by making cuts in the panel. As illustrated, below support member 24, the panel has been cut to form a flap 25, through which the suture 21 is placed. The flap 25 tends to hold the suture in place until removed by the operating room personnel. Above support member 24, the panel has been cut to form an oblong opening 26.

Similarly, above support member 23, the panel has been cut to form an oblong opening 27, and below support member 23 the panel has been cut to form a flap 28. Preferably, the flap 28 is provided with placement notches 29, in order to guide the placement of the suture in the package, and preferably to hold the suture in a preferred position in the package.

Also depicted in FIG. 2 is a flap 35 which serves as a tail park. This flap can be used to hold the tail of one of the sutures held by the panel 20, and further serves to ensure that there is no entanglement between the sutures held in the package.

It is preferred to provide a sterile suture package which contains a number of panels bearing sutures as illustrated in FIGS. 1 and 2. Preferably the package as provided has all of the sutures needed to perform a sternotomy repair operation.

Figure 4:
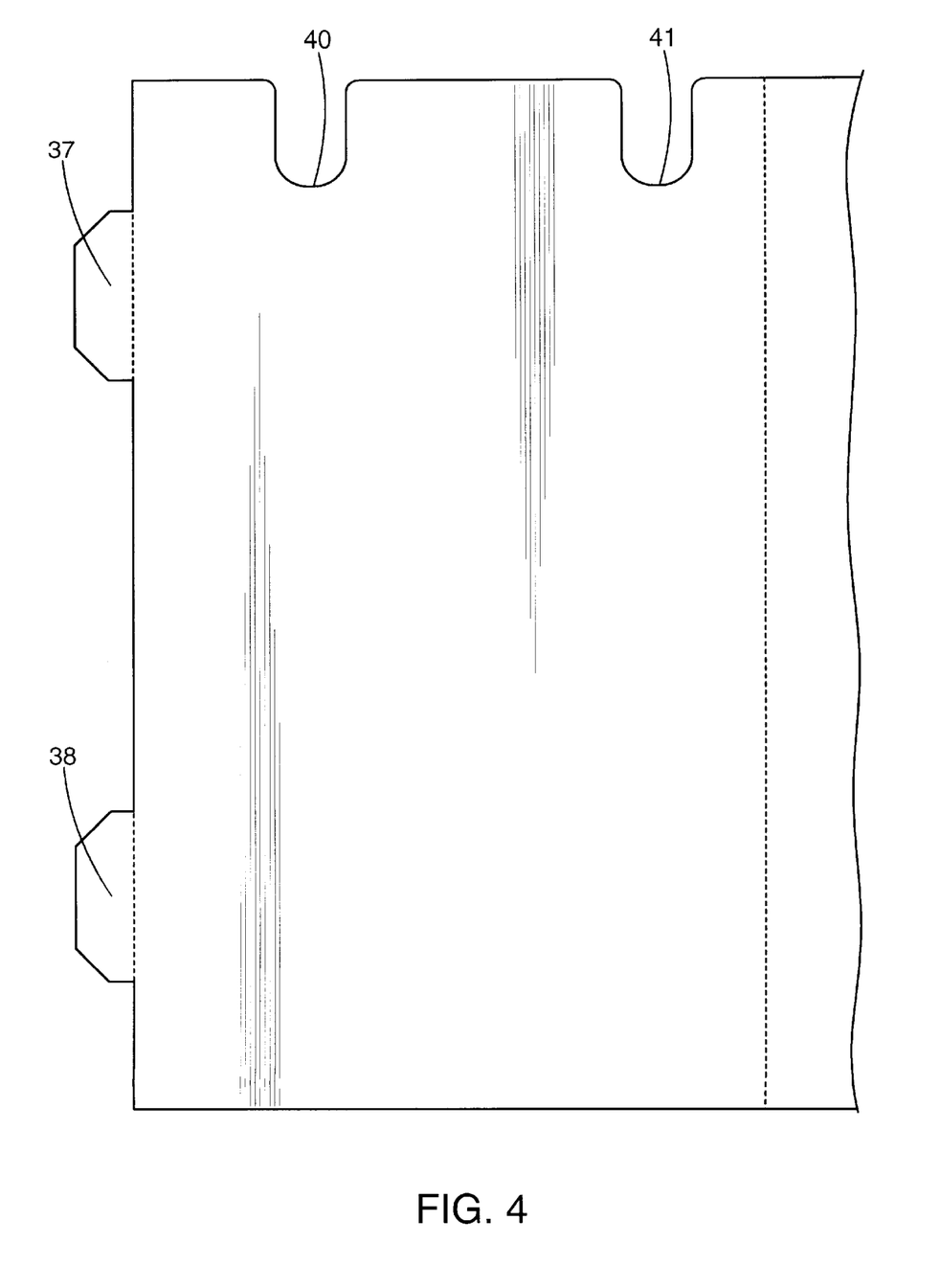
FIG. 4 is a plan view of the inside face of the front cover of a suture package illustrated in FIG. 3.
Figure 5:
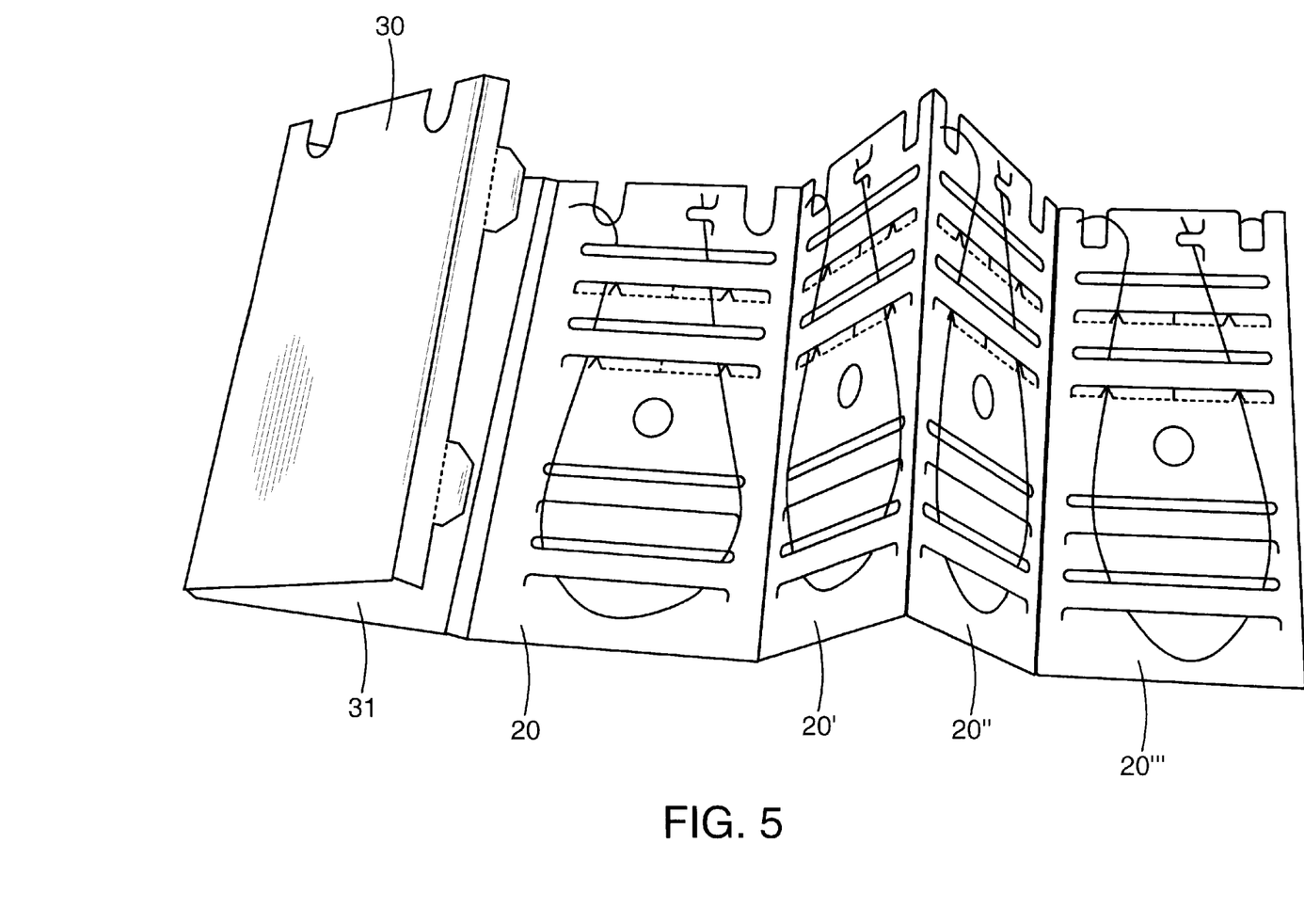
FIG. 5 is a plan view of an opened suture package of the type illustrated in FIGS. 3 and 4.

The preferred package accomplishes the object shown in FIG. 5. The package has a front cover 30, a back cover 31, which is attached to a series of panel suture packages 20, 20', 20" and 20'". The total package is shown in FIG. 5 with the panel suture holders deployed. However, prior to deployment in the operating room, the panels are contained between the front cover 30 and the back cover 31. Preferably the front or back cover has tabs (37 and 38, FIG. 4), and the other cover has slots which fit the tabs, so that the covers can be joined to enclose the suture holding panels until desired deployment. The suture is preferably deployed in the operating room from the closed package.

It is preferred that the panels are perforated along the lines of their joinders to each other and to the cover, so that individual panels can be separated from the overall package, if desired.

It is also preferred that an opening 36 be placed in an area spaced from the sutures, which facilitates sterilization of the package, e.g. by ethylene oxide gas or other sterilizing agent.

It is also preferred that the covers have needle windows 40' and 41', corresponding to the needle windows 40 and 41 on the individual panels, so that, if desired, the sutures and needles can be taken from the sterile package without deploying the individual suture holding cards.

The embodiment depicted and described is only illustrative of the present invention.

The skilled in the art will readily appreciate a variety of embodiments once acquainted with the present disclosure, all of which are intended to be included within the scope of the following claims:

I claim:

1. A suture package, comprising a panel having first and second sides, a first needle window and a plurality of support elements on the first side of the panel, which elements support a suture in conjunction with the panel, the support elements being arranged to permit withdrawal of a suture from the package by pulling one end of the suture in a direction parallel to the plane of the panel; and a second plurality of support members located on a second side of the panel, the second plurality of support members being arranged to support a second suture on the second side of the panel.

2. The suture package of claim 1, wherein the panel is an elongate member having first and second end portions and the first needle window is an opening adjacent to the first end portion thereof and is suitable for placing a finger under a needle for grasping of a needle and withdrawal of a suture from the package.

3. The suture package of claim 1, further comprising a second needle window, spaced from the first needle window.

4. The suture package of claim 1, the panel being sized to permit curving of a stainless steel suture to approximately half its length without substantially adversely effecting the strength of the suture.

5. The suture package of claim 1, further comprising a guide member having guide notches thereon for guiding placement of a suture in the package.

6. The suture package of claim 5, wherein each of the first and second sides of the panel include a guide member having guide notches for guiding placement of a suture.

7. A suture package comprising a plurality of panels, each panel having a plurality of support elements on a first side of the panel and on a second side of the panel, which elements support a first suture on the first side and a second suture on the second side of the panel, the support elements being arranged to permit withdrawal of a suture from the package by pulling one end of the suture in a direction parallel to the plane of the panel.

8. The suture package of claim 7, further comprising a first needle window located in a manner to assist in withdrawing the needle and suture from the package.

9. The suture package of claim 8, wherein the first needle window is an opening adjacent to an end portion of the panel that is suitable for placing a finger under a needle for grasping of a needle and withdrawal of a suture from the package.

10. The suture package of claim 7, wherein each panel further comprises a second plurality of support members and a second needle window located on the second side of the panel, the second plurality of support members being arranged to support a second suture on the second side of the panel and the second needle window located in a manner to assist in withdrawing a second needle and suture from the package.

11. The suture package of claim 7, wherein each panel further comprises a first needle window and a second needle window wherein the second needle window is spaced from the first needle window.

12. The suture package of claim 8, the package being sized to permit curving of a stainless steel suture to approximately half its length without substantially adversely effecting the strength of the suture.

13. The suture package of claim 7, the package being sized to permit curving of a stainless steel suture to approximately half its length without substantially adversely effecting the strength of the suture on the first side and the second side of the panel.

14. The suture package of claim 1, wherein each panel further comprises a guide member having guide notches for guiding placement of a suture in the package.

15. The suture package of claim 1, wherein the sutures contained in the package are not subjected to a curvature smaller than about 1 inch.

16. The suture package of claim 15, wherein the sutures contained in the package are not subjected to a curvature smaller than about 1.5 inches.

17. The suture package of claim 7, wherein the first side and second side of each panel further comprises a guide member having guide notches for guiding placement of a suture in the package.

18. The suture package of claim 7 wherein the sutures contained in the package are not subjected to a curvature smaller than about 1 inch.

19. A suture package, comprising an elongate panel having first and second sides, first and second end portion, first and second needle windows and a first plurality of support elements on the first side of the panel, which elements support a suture in conjunction with the panel, the support elements being arranged to permit withdrawal of a suture from the package by pulling one end of the suture in a direction generally parallel to the plane of the panel;

a second plurality of support members located on a second side of the panel, the second plurality of support members being arranged to support a second suture on the second side of the panel;

wherein the first and second needle windows are openings located adjacent to the first end portion thereof and are suitable for placing a finger under a needle for grasping of a needle and withdrawal of a suture from the package and the second needle window is spaced from the first needle window; and wherein each of the first and second sides of the panel each include a guide member having guide notches for guiding placement of a suture.

20. The suture package of claim 19 wherein the first plurality of the support elements on the first side of the panel are located adjacent to the second plurality of support elements.

21. The suture package of claim 19 wherein the first plurality of the support elements on the first side of the panel extend laterally from the first side of the panel and the second plurality of support elements extend laterally from the second side of the panel.

* * * * *